(12) United States Patent
Downey

(10) Patent No.: US 6,880,557 B2
(45) Date of Patent: Apr. 19, 2005

(54) BREATHING METHOD AND APPARATUS

(75) Inventor: Brendan Michael Downey, Queensland (AU)

(73) Assignee: Fahrenheit 212 Limited, Auckland (NZ)

(*) Notice: Subject to any disclaimer, the term of this patent is extended or adjusted under 35 U.S.C. 154(b) by 102 days.

(21) Appl. No.: 10/148,802

(22) PCT Filed: Dec. 6, 2000

(86) PCT No.: PCT/NZ00/00240

§ 371 (c)(1),
(2), (4) Date: Jun. 5, 2002

(87) PCT Pub. No.: WO01/39837

PCT Pub. Date: Jun. 7, 2001

(65) Prior Publication Data

US 2002/0170561 A1 Nov. 21, 2002

(30) Foreign Application Priority Data

Dec. 6, 1999 (NZ) .............................................. 501564

(51) Int. Cl.$^7$ ............................................. A62B 23/02
(52) U.S. Cl. .............................. 128/205.28; 128/200.24
(58) Field of Search .... 604/58–60; 128/200.14–200.24, 128/201.26, 202.12, 202.21, 203.12, 203.23, 205.11, 205.12, 205.24, 205.27–205.29, 207.14, 207.16, 201.25; 600/527–543

(56) References Cited

U.S. PATENT DOCUMENTS

| 4,086,923 A | | 5/1978 | Henkin | |
| 4,210,137 A | | 7/1980 | Henkin | |
| 4,275,722 A | | 6/1981 | Sorensen | |
| 4,325,364 A | | 4/1982 | Evans | |
| 4,334,533 A | * | 6/1982 | Henkin | 128/205.28 |
| 5,007,421 A | * | 4/1991 | Stewart | 128/204.18 |
| 5,109,837 A | * | 5/1992 | Gamow | 128/202.12 |
| 5,154,167 A | | 10/1992 | Hepburn | |
| 5,398,678 A | * | 3/1995 | Gamow | 128/205.26 |
| 5,471,978 A | | 12/1995 | Yoshida et al. | |
| 5,551,416 A | * | 9/1996 | Stimpson et al. | 128/200.16 |
| 5,647,345 A | * | 7/1997 | Saul | 128/201.23 |
| 5,850,833 A | | 12/1998 | Kotlair | |
| 6,125,843 A | * | 10/2000 | Gold et al. | 128/200.23 |

FOREIGN PATENT DOCUMENTS

| EP | 0 238 463 A1 | 9/1987 |
| RU | 2040279 C1 | 7/1995 |
| RU | 2070064 C1 | 12/1996 |

\* cited by examiner

*Primary Examiner*—Glenn K. Dawson
(74) *Attorney, Agent, or Firm*—Young & Thompson

(57) ABSTRACT

A breathing apparatus (10) including a mouthpiece (13) and a carbon dioxide removal area (18) disposed between the mouthpiece and an air reservoir chamber (19). The chamber is preferably filled with a foam material (27) and is further in communication with ambient air (29) to enable mixing with expired air within the chamber (19). The breathing apparatus (10) is useful for simulating the lower partial pressure of oxygen at high altitude, hence it may be used by athletes for simulating "living at altitude".

16 Claims, 4 Drawing Sheets

BREATHING METHOD AND APPARATUS

BACKGROUND TO THE INVENTION

This invention relates to a breathing method and apparatus.

More particularly, this invention relates to a portable altitude simulator method and apparatus. By use of the invention the user employing the breathing method and apparatus can inspire air having a lower partial pressure of oxygen than the ambient air so as to simulate an altitude which is elevated with respect to where the method and apparatus is being employed. Thus, for example, a user can become acclimatised to higher altitude before travelling to a place of higher altitude or for performance training or sporting activities or medical applications.

In the 1970s it was thought that if an athlete trained and lived at altitude then the athlete would perform better at both sea level and at altitude. However, it is now the general opinion of sports scientists, athletes and coaches that living and training at altitude might not be helpful for performance at sea level. The present trend is therefore to live at altitude (live high) and train at sea level (train low). This has been proven to be the best set-up for maximising the benefits of altitude.

As a consequence the live high/train low model has received good deal of attention from research sports scientists and athletes and coaches. One significant problem with this model is that travel time from the top of a mountain (say, greater than 3000 metres) to sea level (or near sea level, e.g. less than 1000 metres) can impact on recovery and lessen or indeed negate the benefit of living high. A further problem is that if the athlete lives a long way from any mountain suitable to live high, the athlete cannot obtain the desire benefit. It is also a well known medical fact that altitude exposure is beneficial for improving breathing in many medical conditions.

Apparatus to generate a lower partial pressure of oxygen than ambient air, and thereby simulate altitude, are known, e.g. U.S. Pat. No. 4,086,923. However, such devices are generally complex, including valve arrangements etc.

SUMMARY OF THE INVENTION

The object of the present invention is to provide a portable breathing method and apparatus which enables a user to conveniently simulate living at altitude. It is a preference for the portable apparatus to be simple to construct and operate.

Broadly, according to one aspect of the invention, there is provided a breathing apparatus including a container, mouthpiece means opening into the container, carbon dioxide removal means disposed in an airflow between the mouthpiece means and an air reservoir means, the air reservoir means being disposed at least partially between the removal means and an ambient air inlet, means to adjust the effective volume of the air reservoir means whereby air expirated from a user can flow through the removal means into the reservoir means and mix with ambient air, such mixture to be inspired by the user through said mouthpiece via said removal means.

In a second broad aspect of the invention there is provided a method of breathing including the steps of expirating air through carbon dioxide removal means into a reservoir means that is coupled with an ambient air inlet, the effective volume of said reservoir means being adjustable by moving the inlet in relation to the removal means.

Broadly according to a third aspect there is provided a breathing apparatus including a mouthpiece, an inlet port for ambient air, a carbon dioxide removal means disposed in an air flow between the mouthpiece and a chamber including a foam material there within, said chamber being disposed at least partially between the removal means and the inlet port, and wherein air expirated through said mouthpiece/removal means by a user is mixed with ambient air in the chamber and inspired back through the same removal means/mouthpiece.

In a preferred form of the invention the inlet/exhaust port means is an opening into the chamber, the position of the opening being adjustable.

According to a second form the inlet/exhaust port means is a plurality of openings, there being closure means to selectively close all but one of the openings, the openings being spaced at different distances from the removal means.

In a further form of the invention additional foam filled chambers may be coupled to the (first) chamber to increase the effective distance between the mouthpiece and the inlet/exhaust port means.

Preferably the removal means is soda lime.

Preferably the mouthpiece means is adjustable in position. Accordingly to a preferred form the mouthpiece means is pivotally coupled to a cap which is removably mounted to an open end of the container.

DESCRIPTION OF THE PREFERRED EMBODIMENT

Figure 1:
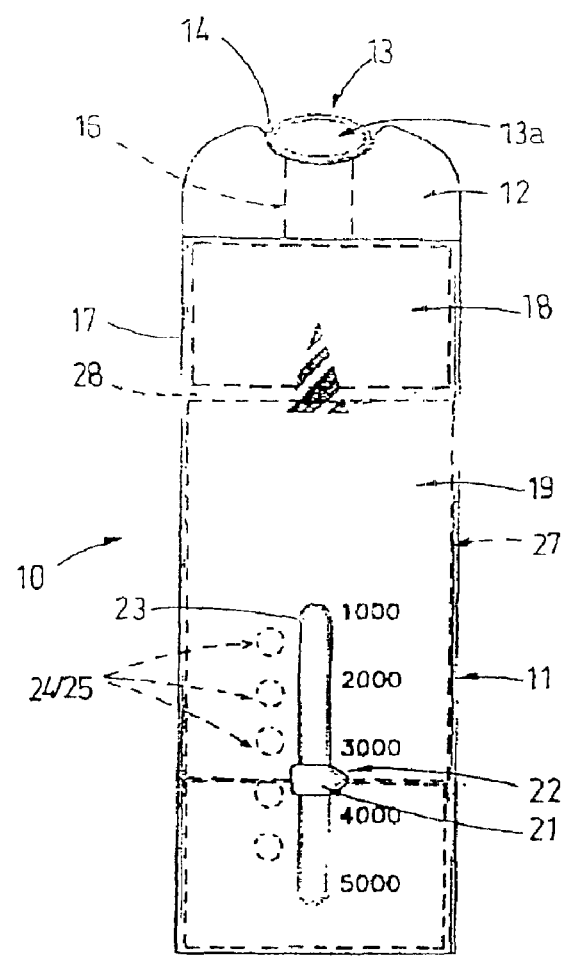
FIG. 1 is a front elevation view of the apparatus.

The apparatus 10 according to one form of the invention and as shown in FIG. 1 is a portable device which enables a user to conveniently breathe through the apparatus so as to simulate breathing at an altitude. By use of the apparatus, the user is able to assimilate living at altitude and therefore become conditioned to the lower oxygen present at high altitudes. As will hereinafter become apparent, the portability of the apparatus enables the user to breathe through the apparatus during normal activity, however, any training activities would be conducted without use of the apparatus.

As shown in FIG. 1, the apparatus in a first form is in the form of an open-ended canister 11 with a removable top 12 mounted on the open end. This can be a screw-on cap though clearly other attachment means can be used such as clip-on, interference fit, etc. A mouthpiece 13 having an open or outlet end 13a is located within a recessed portion 14 of the top 12.

Figure 2:
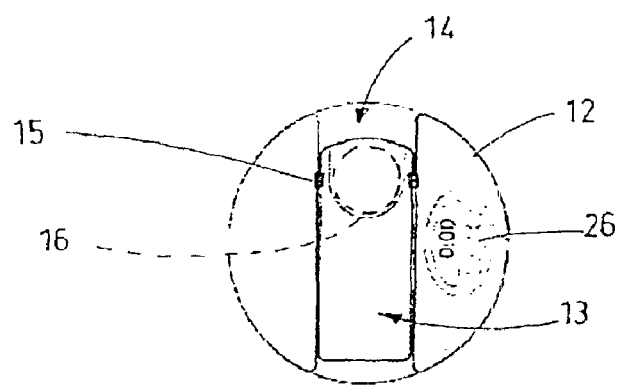
FIG. 2 is a top plan view of the apparatus.
Figure 3:
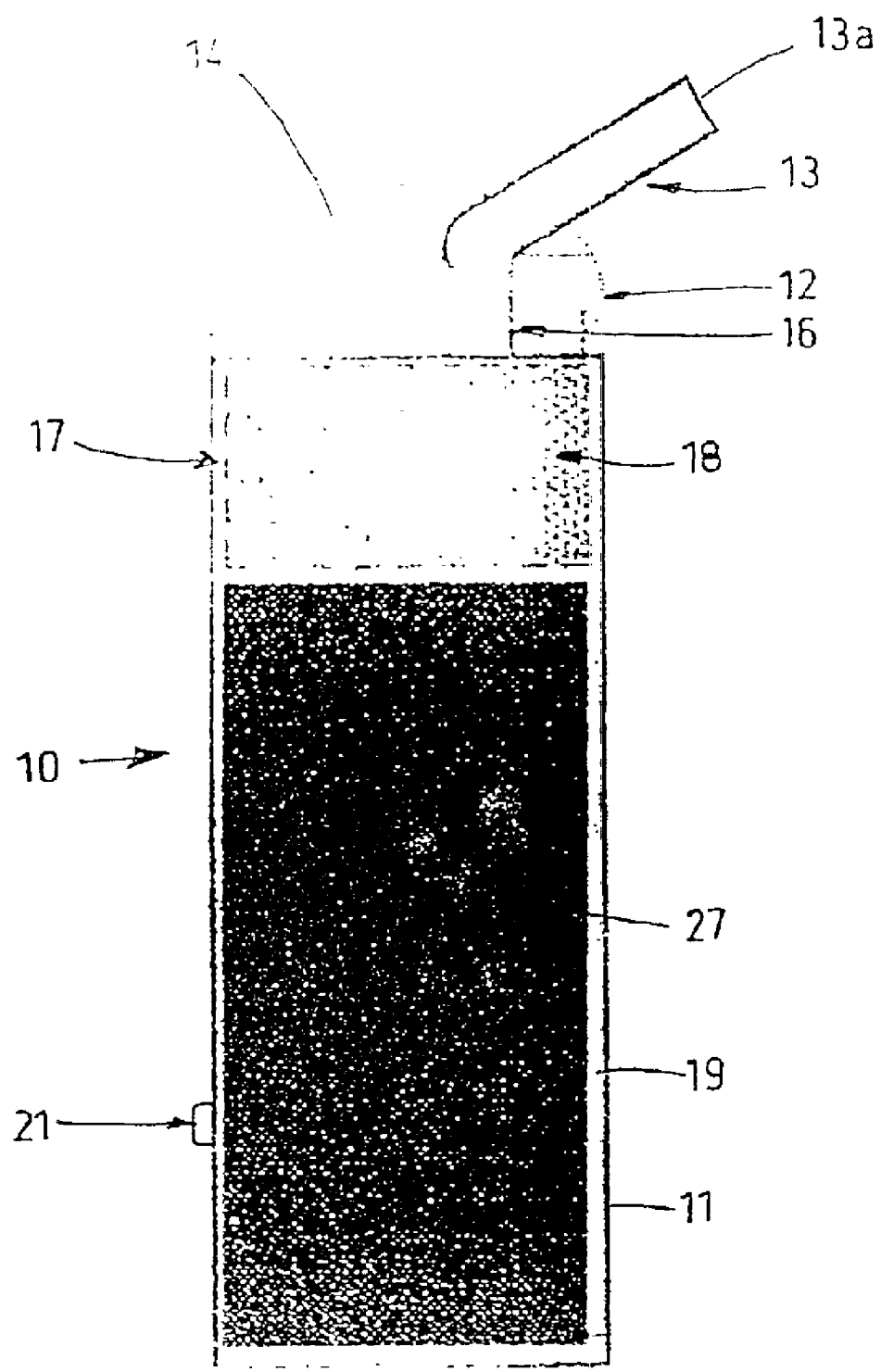
FIG. 3 is a sectioned cross-sectional elevation view of the apparatus.

As best illustrated by FIG. 2, the mouthpiece 13 is pivotally mounted by pivot 15. This enables the mouthpiece 13 to be moved from the rest position as shown in the drawings to an elevated position. In the elevated position a user can place his or her mouth over the outlet end 13a of the mouthpiece 13.

In an alternative arrangement (described hereinafter) a flexible hose or other conduit could be attached by any suitable means (including a simple push-on attachment) to the outlet end 13a of the mouthpiece 13. The other end of the hose would have a mouthpiece which could be engaged in or around the mouth and/or nose of the user.

It will be appreciated by those skilled in the art that other arrangements could be used to facilitate the user breathing through the apparatus as will hereinafter be described. For example, rather than a mouthpiece at the distal end of a hose coupled to mouthpiece 13, a mask or similar could be provided which could be held over the user's mouth in any known manner such as, say, an elastic element which fits about the user's head.

The mouthpiece 13 communicates via the passageway formed by breather tube 16 with a chamber formed by the interior of canister 11. The chamber is effectively divided into a first chamber part 17 and a second chamber part 19. This second chamber part 19, as will hereinafter become apparent, effectively acts as a reservoir for a mix of expired air and ambient air.

In the first chamber part 17 is located carbon dioxide scrub material 18. Chamber part 17 communicates via partition 28 with chamber part 19. The partition 28 preferably has a plurality of openings or passageways through which air can pass. In a convenient arrangement, the partition 28 can be formed by a foam material or a mesh. However, this partition 28 may in some arrangements not be required.

The altitude to be simulated is adjustable. This is achieved by adjusting the effective volume of ambient air added to expired air in second chamber part 19. This chamber part 19 effectively acts as a reservoir and mixing chamber in which ambient or new air can mix with expired air. Thus, an inlet arrangement is provided in the wall of the canister 11 so that air can enter chamber 19 to mix with expired air already within the chamber, the mixture of expirated and ambient air then being able to be drawn back through the carbon dioxide removal material 18 to be breathed in by the user.

Therefore, the effective unit volume of air being supplied for inspiration by the user has a lesser oxygen content than the ambient air. This results in simulation of altitude above ambient.

In the preferred form of the invention second chamber part 19 is fitted with foam material 27 to regulate airflow through the device. For simplicity of construction partition 28 can be omitted and the scrub material is simply supported by the foam material 27.

According to the preferred form of the invention, adjustment means are provided whereby the simulated altitude can be adjusted. With reference to FIG. 1 this can be achieved by adjusting the "altitude gauge" 22 (and therefore an associated inlet/exhaust port) up and down to different positions. As a result the volume of retained aspirated air to incoming ambient air can be increased as the simulated altitude increases. This is achieved because the amount of air inside the foam below the level of the inlet/exhaust port will not mix to any great extent.

The gauge 22 can be moved up and down to a desired position by an externally accessible operator button, knob or the like 21 which is slidingly engaged within an elongate longitudinally aligned slot 23. The air inlet/exhaust port (to enable air Lo exhaust from and ambient air to enter the mixing chamber 19) can be an opening which moves with the knob 21 such that It always communicates with the chamber 19 as different positions dependent on the position of the knob 21.

Alternatively, a series of openings 24 (shown in dotted detail) could be provided in the wall of the canister 11. Each of these openings 24 would be closed by removable plug 25. The user would then remove the plug from the opening 24 adjacent the altitude marking indicating the altitude being simulated. Thus, for example, to simulate an altitude of 3000 metres the plug would be removed from the opening 24 adjacent the 3000 metre indicator.

Other means of adjusting the mixing chamber volume and at the same time ensuring an inlet for ambient air into the chamber will be apparent to those skilled in the art.

Figure 4:
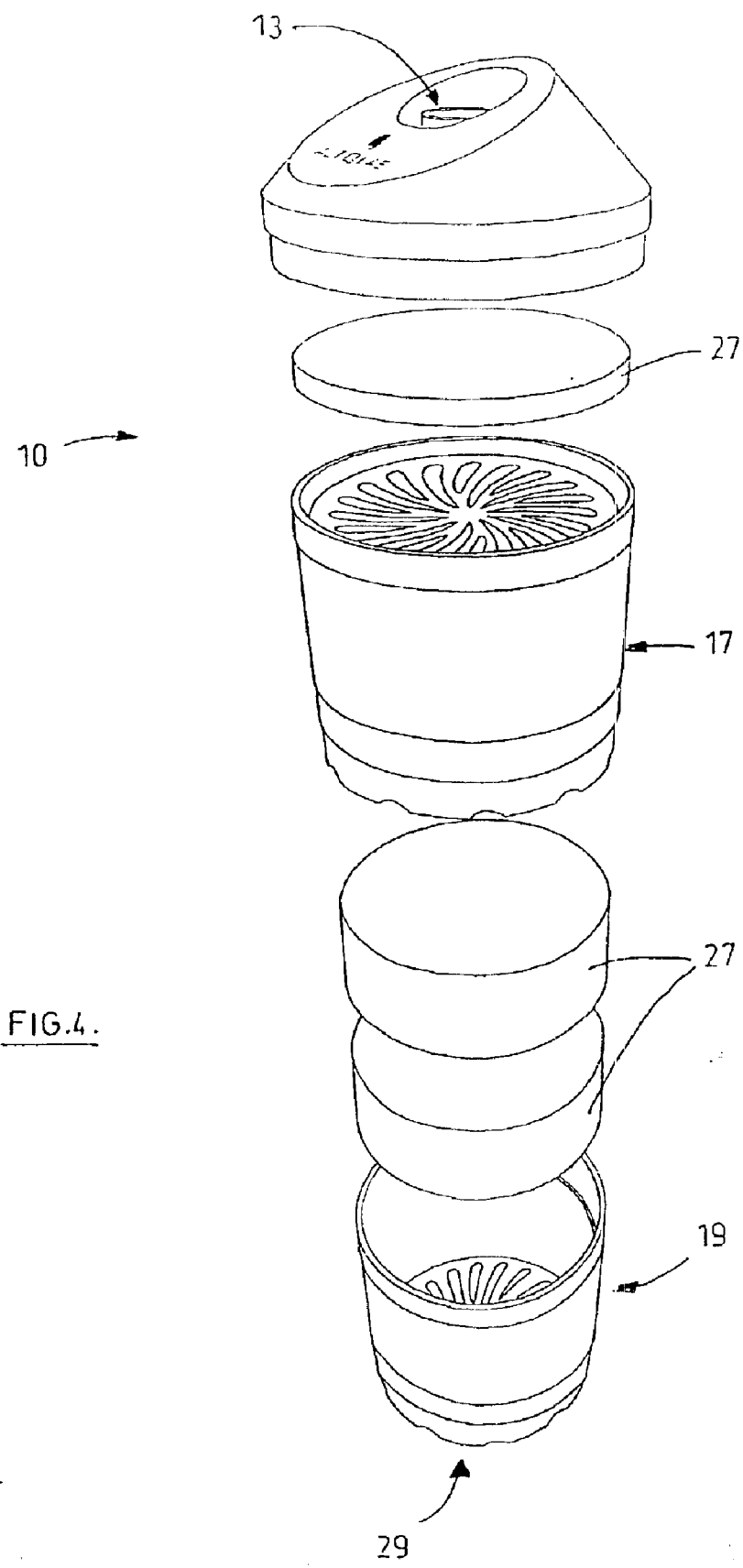
FIG. 4 is an exploded perspective view of a preferred embodiment of the apparatus.
Figure 5:
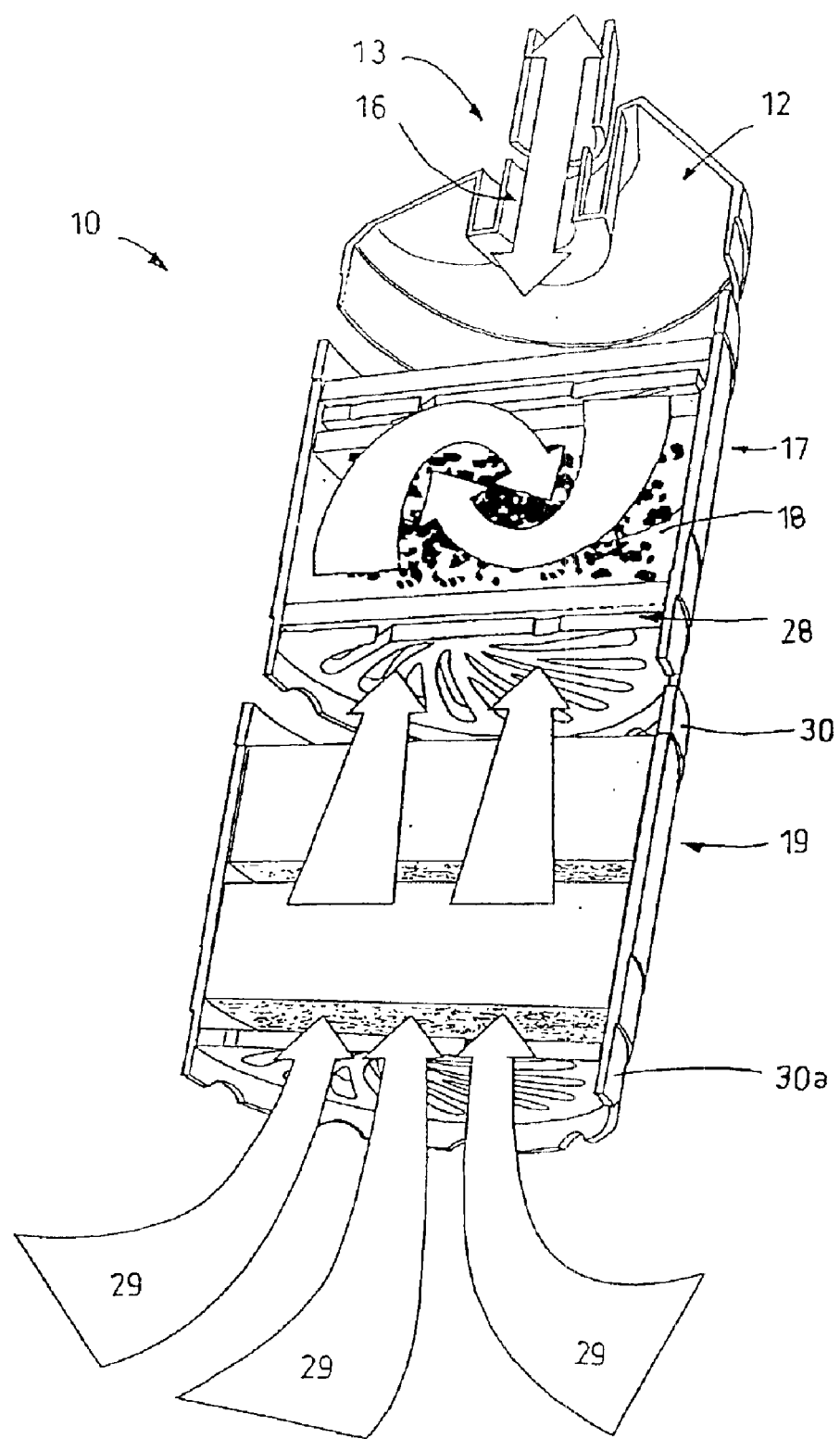
FIG. 5 is a sectional perspective view of the preferred embodiment.

FIGS. 4 and 5 illustrate a further preferred embodiment of the invention wherein the same reference numerals have been used where possible.

FIG. 4 illustrates an exploded view wherein all foam inserts are denoted 27. The two chambers 17, 19 are if n this embodiment, separate 'modules' that may be fitted together end-to-end, e.g. in an interference or click fit.

Module 17 includes carbon dioxide removal means 18 as previously. Removal means 18 is readily accessible, due to the modular nature of the apparatus, and may be replaced or reconditioned as necessary.

Module 19 includes (in the illustrated form) two foam filters 27 that restrict air flow through the apparatus from the intake 29 below.

The effective volume is adjustable by adding or removing foam filters 27 or, preferably, fitting additional modules 19 (by interference fit at areas 30 and 30a). Additional modules 19 will thereby make the whole apparatus 10 longer than illustrated. Increasing the number of modules 19 in series increases the simulated altitude as there is a greater distance (through the foam 27) between the mouthpiece 13 and the inlet/exhaust 29.

According to a preferred form of the invention so that the apparatus is readily portable, the total volume of the canister could be up to 5000 mL though more particularly between about 500 and 2000 mL. The amount of carbon dioxide scrub material 18 could then be in the order of 10014 500 g when soda lime is used. Scrub materials other than soda lime could be used. In a further arrangement a smaller device could be provided with a smaller chamber 18 having a carbon dioxide absorbent material.

Dependent on the density of foam 27, the size of chamber 19 could also be reduced. The preferred product specification of foam is 23105. The density of this foam is 23 kg/m$^3$ with a hardness factor of 105N.

Other modifications will be apparent to those skilled in the art. For example, the apparatus in a less preferred form could include a balloon or bag that fills up with some of the expired air on expiration and then empties on inhalation. Such an arrangement could further reduce the size of the apparatus.

In a further arrangement, the device could be made disposable. If economical production costs can be realised the device could be used, say, four times and then thrown away in the trash. However, the device would be reusable by replacing the carbon dioxide scrubber/absorber material 18 as required.

According to other forms of the apparatus useable ancillary equipment can be provided. For example, it may be useful to provide lid 12 with a built in time means 26. Thus, the user can set the timer 26 so that when it times out a visual or audible signal can be set off. This will enable the user to establish a time limit for ending use of the apparatus.

A compact portable apparatus which can be used to simulate breathing at altitude is thus achievable by the present invention. This is achieved by passing air expired and inspirated by the user through the carbon dioxide scrubber/absorber material. Thus, air passes through the material on both inhalation and exhalation. This results in a compact device and indeed one which could be disposable in nature.

It is believed that the apparatus herein described is considerably simpler to construct and operate than other altitude simulation apparatus. Consequent cost savings will make the apparatus more widely available for athletic training.

What is claim is:

1. A breathing apparatus (10) including a container (11), mouthpiece means (13) opening into the container, carbon dioxide removal means (18) disposed in an air flow between the mouthpiece means and an air reservoir means (19), the air reservoir means being disposed at least partially between the removal means (18) and an ambient air inlet (24), means to adjust the effective volume of the air reservoir means (19), wherein air expirated from a user flows through the removal means into the reservoir means and mix with ambient air, such mixture to be inspired by the user through said mouthpiece (13) via said removal means (18).

2. The breathing apparatus of claim 1, wherein the removal means (18) is soda lime.

3. The breathing apparatus of claim 1 wherein the mouthpiece means (13) is pivotally coupled to a cap (12).

4. The breathing apparatus of claim 1 wherein the mouthpiece means (13) includes an elongate conduit means for distally locating the breathing apparatus relative to a user.

5. A method of breathing including the steps of expirating air through carbon dioxide removal means (18) into a reservoir means (19) that is coupled with an ambient air inlet (24), the effective volume of said reservoir means (19) being adjustable by moving the inlet (24) in relation to the removal means (18), and inspiring air from said reservoir means through said carbon dioxide removal means.

6. The breathing apparatus of claim 5, wherein the removal means (18) is soda lime.

7. A breathing apparatus (10) including a mouthpiece (13), an inlet port (24, 29) for ambient air, a carbon dioxide removal means (18) disposed in an air flow between the mouthpiece (13) and a chamber (19) including a foam material (27) therewithin, said chamber being disposed at least partially between the removal means (18) and the inlet port (24, 29), and wherein air expirated through said mouthpiece/removal means by a user is mixed with ambient air in the chamber (19) and inspired back through the same removal means/mouthpiece.

8. The breathing apparatus of claim 7 wherein the inlet port (24,29) is an opening directly into the chamber (19).

9. The breathing apparatus of claim 8 wherein the distance of the inlet port relative to the removal means (18) is adjustable.

10. The breathing apparatus of claim 8 wherein the inlet port (24/29) is a plurality of openings, there being closure means (25) to selectively close all but one of the openings, the openings being spaced at different distances from the removal means (18).

11. The breathing apparatus of claim 7 wherein the inlet port (24/29) is an opening in a wall of the chamber (19) furthest from the removal means (18) to communicate with ambient air (29).

12. The breathing apparatus of claim 7 wherein a second chamber including foam material (27) therewithin may be coupled to the chamber (19) and covering the inlet port (24/29) to communicate therebetween, and including a further inlet port means in the second chamber to communicate with ambient air.

13. The breathing apparatus of claim 12 wherein further chambers including foam material (27) therewithin may be coupled in series to the second and subsequent chambers communicating therebetween via inlet port means, a last chamber including inlet port means to communicate with ambient air.

14. The breathing apparatus of claim 7, wherein the removal means (18) is soda lime.

15. The breathing apparatus of claim 7 wherein the mouthpiece (13) is pivotally coupled to a cap (12).

16. The breathing apparatus of claim 7 wherein the mouthpiece (13) includes an elongate conduit means for distally locating the breathing apparatus relative to a user.

* * * * *